(12) United States Patent
Fodor, Sr.

(10) Patent No.: US 11,819,442 B2
(45) Date of Patent: Nov. 21, 2023

(54) ORTHOTIC CLUBFOOT DEVICE AND METHOD

(71) Applicant: D-BAR ENTERPRISES, LLC, Webster Groves, MO (US)

(72) Inventor: Joe E. Fodor, Sr., Fenton, MO (US)

(73) Assignee: D-Bar Enterprises, LLC, Webster Groves, MO (US)

( * ) Notice: Subject to any disclaimer, the term of this patent is extended or adjusted under 35 U.S.C. 154(b) by 589 days.

(21) Appl. No.: 16/886,240

(22) Filed: May 28, 2020

(65) Prior Publication Data

US 2021/0369483 A1    Dec. 2, 2021

(51) Int. Cl.
*A61F 5/01* (2006.01)
*A61F 5/14* (2022.01)
*A61F 5/37* (2006.01)

(52) U.S. Cl.
CPC .............. *A61F 5/14* (2013.01); *A61F 5/0111* (2013.01); *A61F 5/0116* (2013.01); *A61F 5/3715* (2013.01); *A61F 2005/0158* (2013.01); *A61F 2005/0165* (2013.01); *A61F 2005/0167* (2013.01); *A61F 2005/0179* (2013.01)

(58) Field of Classification Search
CPC ........ A61F 5/0111; A61F 5/0116; A61F 5/14; A61F 5/3715; A61F 2005/0151; A61F 2005/0158; A61F 2005/0165; A61F 2005/0167; A61F 2005/0179; A61F 2005/0197

See application file for complete search history.

(56) References Cited

U.S. PATENT DOCUMENTS

| | | | |
|---|---|---|---|
| 5,346,463 A * | 9/1994 | Devens | A61F 5/0193 604/24 |
| 9,872,789 B2 * | 1/2018 | Sorrenti | A63B 23/08 |
| 10,226,373 B1 * | 3/2019 | McCoy | A61F 5/0125 |
| 10,271,983 B2 * | 4/2019 | Morris | A61F 5/0127 |
| 10,470,914 B2 * | 11/2019 | Powell | A61F 5/013 |

\* cited by examiner

*Primary Examiner* — Keri J Nelson
(74) *Attorney, Agent, or Firm* — Lewis Rice LLC

(57) ABSTRACT

A dual-adjustable orthotic device to treat clubfoot and methods for using same. The device comprises a pair of paddles, adapted to attach footwear, attached at opposing ends of an adjustable torque bar the device has independent configuration systems to adjust the angle at which the paddles are oriented to the bar, and to adjust the torque loading applied to the paddles. These systems facilitate the independent adjustment of the device settings without changing the tensioning mechanism, stocking multiple devices, or having to disassemble and reassemble the tensioning structures.

9 Claims, 5 Drawing Sheets

ORTHOTIC CLUBFOOT DEVICE AND METHOD

BACKGROUND OF THE INVENTION

Field of the Invention

This disclosure is related to the field of clubfoot therapy. In particular, it relates to a device and method for treatment of clubfoot.

Description of the Related Art

Clubfoot is a relatively common congenital birth defect in which one or both of the feet are rotated inward and/or downward, sometimes so severely that the bottom of the foot faces sideways. Although not painful during infancy, if left untreated, the deformation will remain into adulthood, and can inhibit ordinary ambulatory function. Fortunately, clubfoot is often treatable, typically involving the use of an appliance to stretch and reposition the feet, which gradually realigns the ankle and foot for typical use. Afterwards, a minor surgical procedure, known as a tenotomy, may be used to relieve any residual tightness in the Achilles tendon and allow it to heal at the proper length.

After successful correction, clubfoot patients sometimes exhibit reoccurrence. To prevent or inhibit this, the patient may wear a brace, also sometimes known as "boots and bar," for several years. The brace has footwear attached at opposing ends of an elongated bar. The patient's feet are held in the footwear by fasteners, and the footwear is rotated to and maintained at the desired angle to preserve the correction.

This bracing requires adjustment over the years as the patient grows and gets stronger. The bar may need to be lengthened, the shoes may need to be changed, the angle of the shoes may need adjustment, and the amount of tension applied may need to be increased as the child grows and gains muscle mass. This has historically been accomplished by disassembling the entire device to replace the tensioning mechanism, or stocking multiple devices with different tensionings.

SUMMARY OF THE INVENTION

The following is a summary of the invention in order to provide a basic understanding of some aspects of the invention. This summary is not intended to identify key or critical elements of the invention or to delineate the scope of the invention. The sole purpose of this section is to present some concepts of the invention in a simplified form as a prelude to the more detailed description that is presented later.

Described herein, among other things, is an orthotic device comprising: a torque bar; a paddle; and a housing assembly attached to a first end of the torque bar and having the paddle attached to the housing assembly, the housing assembly comprising: a first adjusting system comprising a first pair of toothed elements intermeshing in a plurality of positions, each position in the plurality corresponding to a rotational angle of the paddle; and a second adjusting system comprising a second pair of toothed elements intermeshing in a second plurality of positions, each position in the second plurality corresponding to an amount of torque applied to the paddle.

In an embodiment, the orthotic device further comprises a torsion spring disposed within the housing assembly and applying the amount of torque.

In another embodiment, the first adjustable system and the second adjusting system are independently adjustable.

In an embodiment, the orthotic device further comprises: a second housing assembly affixed to a second end of the torque bar opposing the first end, the second housing assembly having a second paddle attached thereto, the second housing assembly and second paddle being a mirror image of the housing assembly.

In another embodiment, the torque bar has an adjustable length.

In another embodiment, the torque bar comprises two slideably connected bar elements and the adjustable length is adjusted by sliding at least one of the two bar elements.

In another embodiment, the paddle is adapted to attach an orthotic footwear.

In another embodiment, the orthotic footwear is at least one of: a shoe, a boot, and a sandal.

In another embodiment, the orthotic device is a clubfoot correction device.

Also described herein, among other things, is a method for adjusting an orthotic device comprising: providing an orthotic device comprising: a torque bar; a paddle; and a housing assembly affixed to a first end of the torque bar and having paddle attached to the housing assembly, the housing assembly comprising: a first adjusting system comprising a first pair of toothed elements intermeshing in a plurality of positions, each position in the plurality corresponding to a rotational angle of the paddle; and a second adjusting system comprising a second pair of toothed elements intermeshing in a second plurality of positions, each position in the second plurality corresponding to an amount of torque applied to the paddle; intermeshing the first pair of toothed elements in a first position in the plurality of positions, the first position causing the paddle to be oriented to the housing assembly at a first rotational angle corresponding to the first position; disengaging the first pair of toothed elements from each other; rotating at least one toothed element in the first pair of toothed elements to a second position in the plurality of positions, the second position causing the paddle to be oriented to the housing assembly at second rotational angle corresponding to the second position; and intermeshing the first pair of toothed elements in the second position.

In an embodiment, the method further comprises: intermeshing the second pair of toothed elements in a first position in the second plurality of positions, the first position causing a first amount of torque to be applied to the paddle, the first amount of torque corresponding to the first position; disengaging the second pair of toothed elements from each other; rotating at least one toothed element in the second pair of toothed elements to a second position in the second plurality of positions, the second position causing a second amount of torque to be applied to the paddle, the second amount of torque corresponding to the second position; and intermeshing the second pair of toothed elements in the second position.

Also described herein, among other things, is a dual-adjustable housing assembly comprising: a base cap having a first plurality of teeth on a top periphery thereof; a core cap comprising: an inner column; an outer column having a radius larger than the inner column and a height shorter than the inner column, and a top side and an opposing bottom side, the bottom side having a second plurality of teeth on a periphery thereof, the second plurality of teeth intermeshing with the first plurality of teeth; an index ring having a bottom side disposed on the outer column top side so that the inner column passes through the index ring, and an opposing top side having a third plurality of teeth on a periphery thereof;

a torsion spring having a bottom end in connection with the base cap and an opposing top end in connection with the index ring, the torsion ring applying an amount of torque to the index ring, the amount of torque corresponding to a first rotational position of the index ring relative to the base cap; a top cap comprising: a radial protrusion adapted to accept a paddle; and a fourth plurality of teeth on a bottom periphery of the top cap, the fourth plurality of teeth intermeshing with the third plurality of teeth such that the radial protrusion is disposed at a first rotational angle to a vertical axis of the housing assembly, the first rotational angle corresponding to a first rotational position of the top cap relative to the index ring; wherein when the index ring is rotated to a second rotational position relative to the base cap, the torsion spring applies a second amount of torque to the index ring corresponding to the second rotational position of the index ring relative to the base cap; and wherein when the top cap is rotated to a second rotational position relative to the index ring, the radial protrusion rotates to a second rotational angle corresponding to the second rotational position of the top cap relative to the index ring.

In an embodiment, the housing assembly further comprises a wave spring disposed between the index ring and the top cap.

In another embodiment, the housing assembly further comprises: a receiver disposed on the outer column top side; and a locking protrusion extending from the index ring bottom side and disposed in the receiver; wherein the locking protrusion disposed in the receiver causes the index ring and the core cap to rotate in concert.

In another embodiment, the outer column comprises an arcuate aperture.

In another embodiment: a bottom portion of the torsion spring is disposed within a base cap receiver within the base cap interior volume; the bottom end of the torsion spring is disposed within a second receiver within the base cap receiver; a top portion of the torsion spring is disposed within a receiver within an interior volume of the outer column; and the top end passes through the arcuate aperture and is disposed in a receiver in the index ring.

In another embodiment, the arcuate aperture is sized and shaped such that the index ring may be rotated to a plurality of rotational positions relative to the base cap while the top end is disposed through the arcuate aperture.

In another embodiment, the housing assembly further comprises a spring stop disposed in the index ring receiver and the top end of the torsion spring disposed in the spring stop.

Also described herein, among other things, is an orthotic treatment device including the dual-adjustable housing assembly affixed to a first end of a torque bar, and a second dual-adjustable housing assembly affixed to an opposing second end of the torque bar.

In an embodiment, the orthotic treatment device is a clubfoot correction device.

DESCRIPTION OF THE PREFERRED EMBODIMENT(S)

Figure 2:
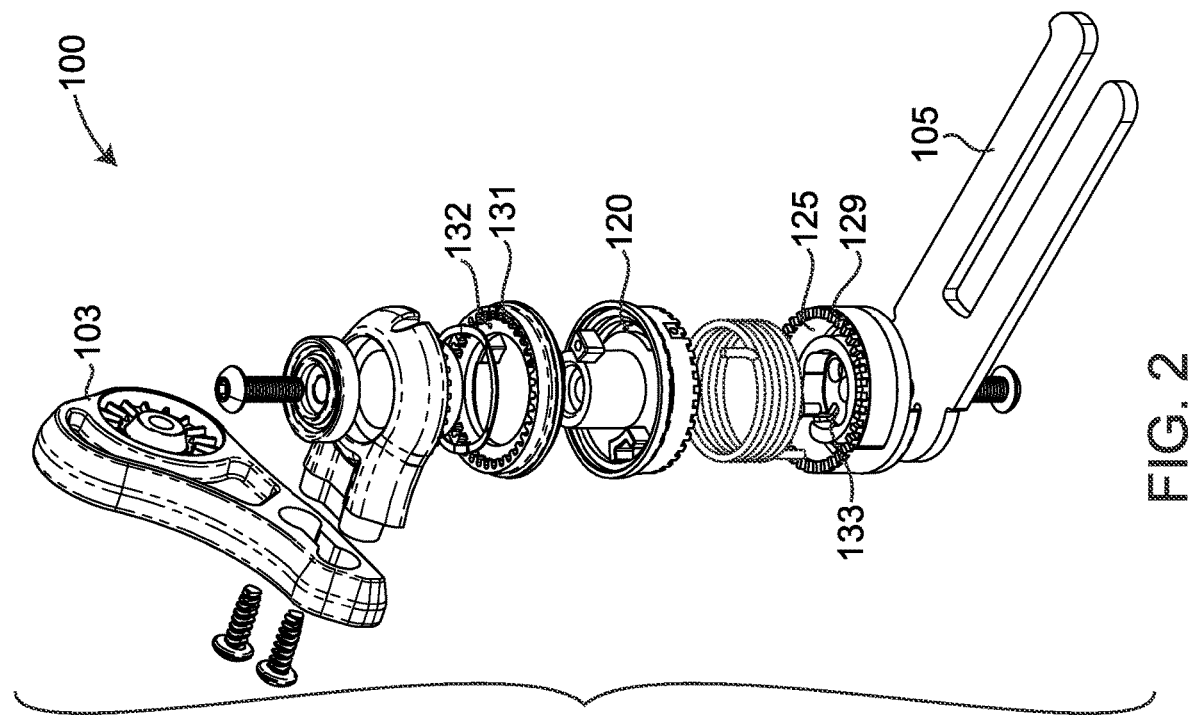
FIG. 2 depicts an exploded isometric view of the device of FIG. 1.

The following detailed description and disclosure illustrates by way of example and not by way of limitation. This description will clearly enable one skilled in the art to make and use the disclosed systems and methods, and describes several embodiments, adaptations, variations, alternatives and uses of the disclosed systems and methods. As various changes could be made in the above constructions without departing from the scope of the disclosures, it is intended that all matter contained in the description or shown in the accompanying drawings shall be interpreted as illustrative and not in a limiting sense.

Described herein, among other things, is a dual-adjustable orthotic device to treat clubfoot and methods for using same. The device comprises a pair of paddles, adapted to attach footwear, the attached at opposing ends of an adjustable torque bar the device has independent configuration systems to adjust the angle at which the paddles are oriented to the bar, and to adjust the torque loading applied to the paddles. These systems facilitate the independent adjustment of the device settings without changing the tensioning mechanism, stocking multiple devices, or having to disassemble and reassemble the tensioning structures.

As can be seen in the depicted embodiments, at high level of generality, the device (100) comprises a pair of paddles (103) attached at opposing ends of a torque bar (105). The paddles (103) comprise a left paddle and a right paddle, which are generally a mirror image of one another, and each includes a surface and/or system or mechanism for attaching footwear, such as a shoe, or for retaining the patient's foot at a desired angle as determined by the orientation of each paddle (103) with respect to the torque bar (105). The paddles (103) are each attached to the torque bar (105) via a housing assembly (107)

Figure 1:
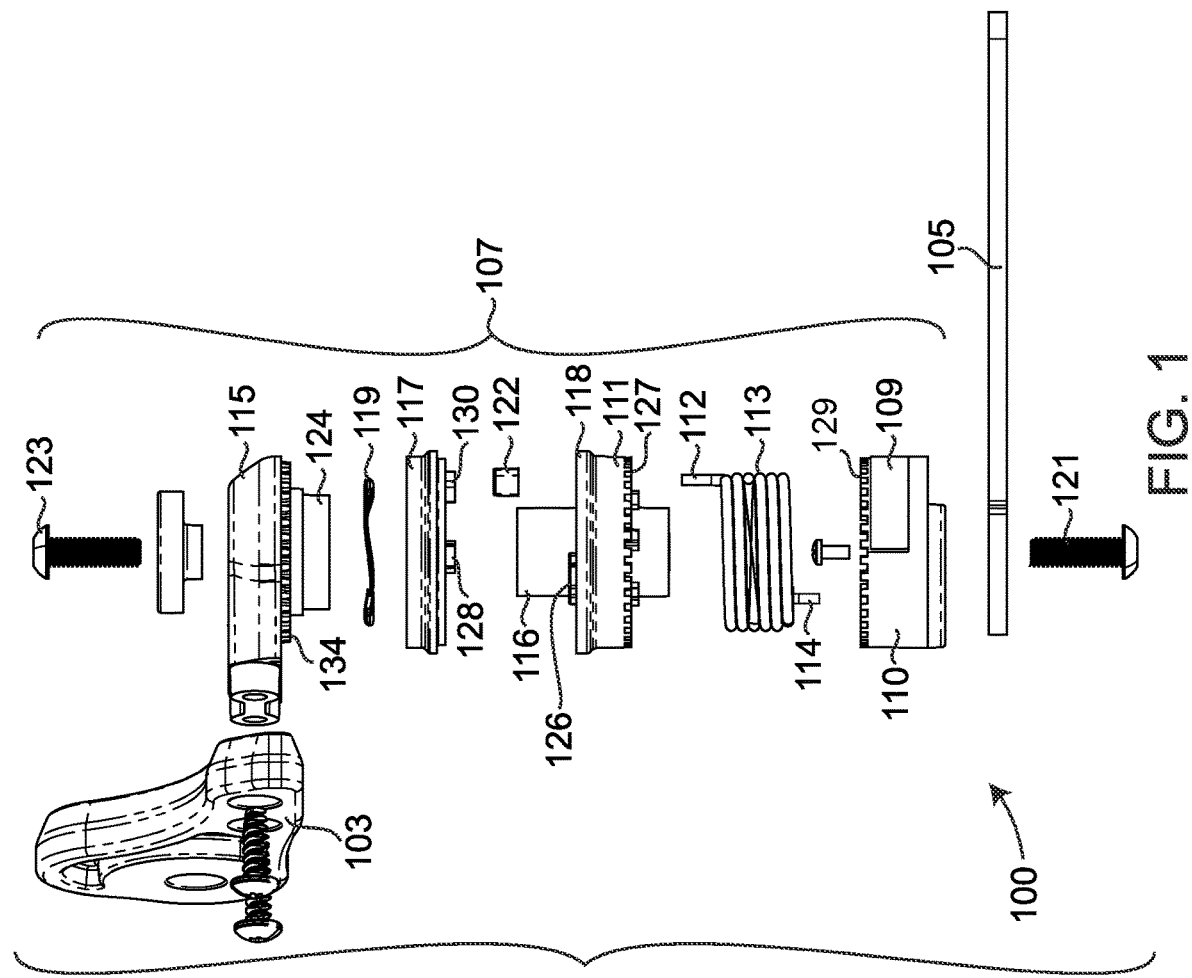
FIG. 1 depicts an exploded elevation view of an embodiment of a dual-adjustable orthotic device according to the present disclosure.
Figure 3:
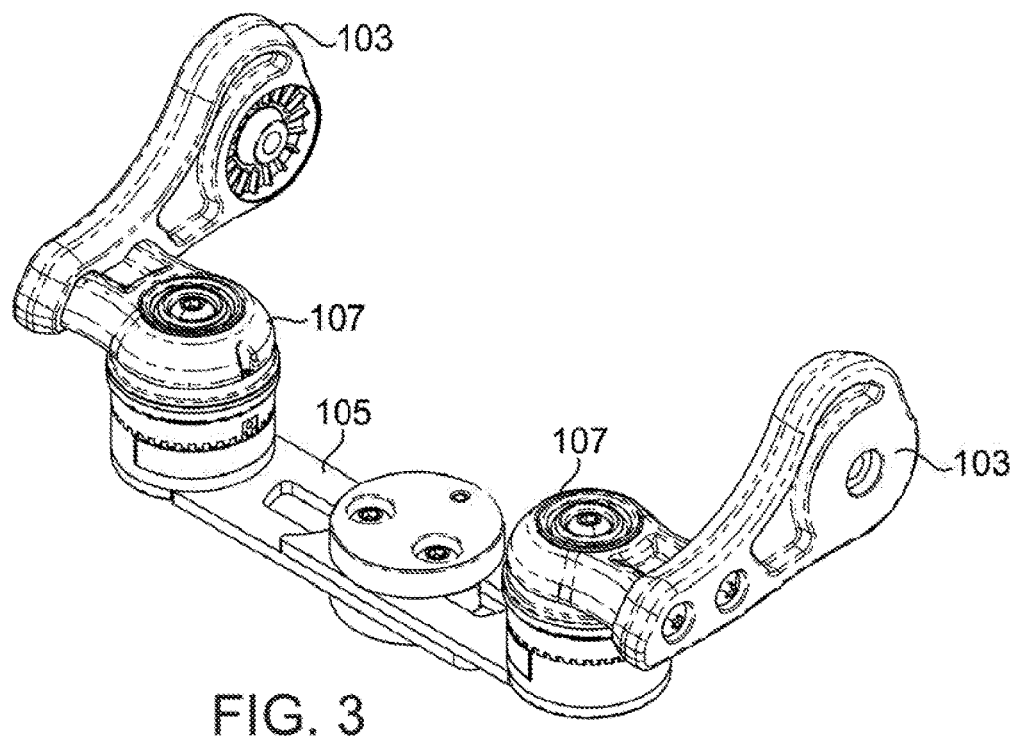
FIG. 3 depicts an assembled view of the device of FIG. 1.
Figure 5A:
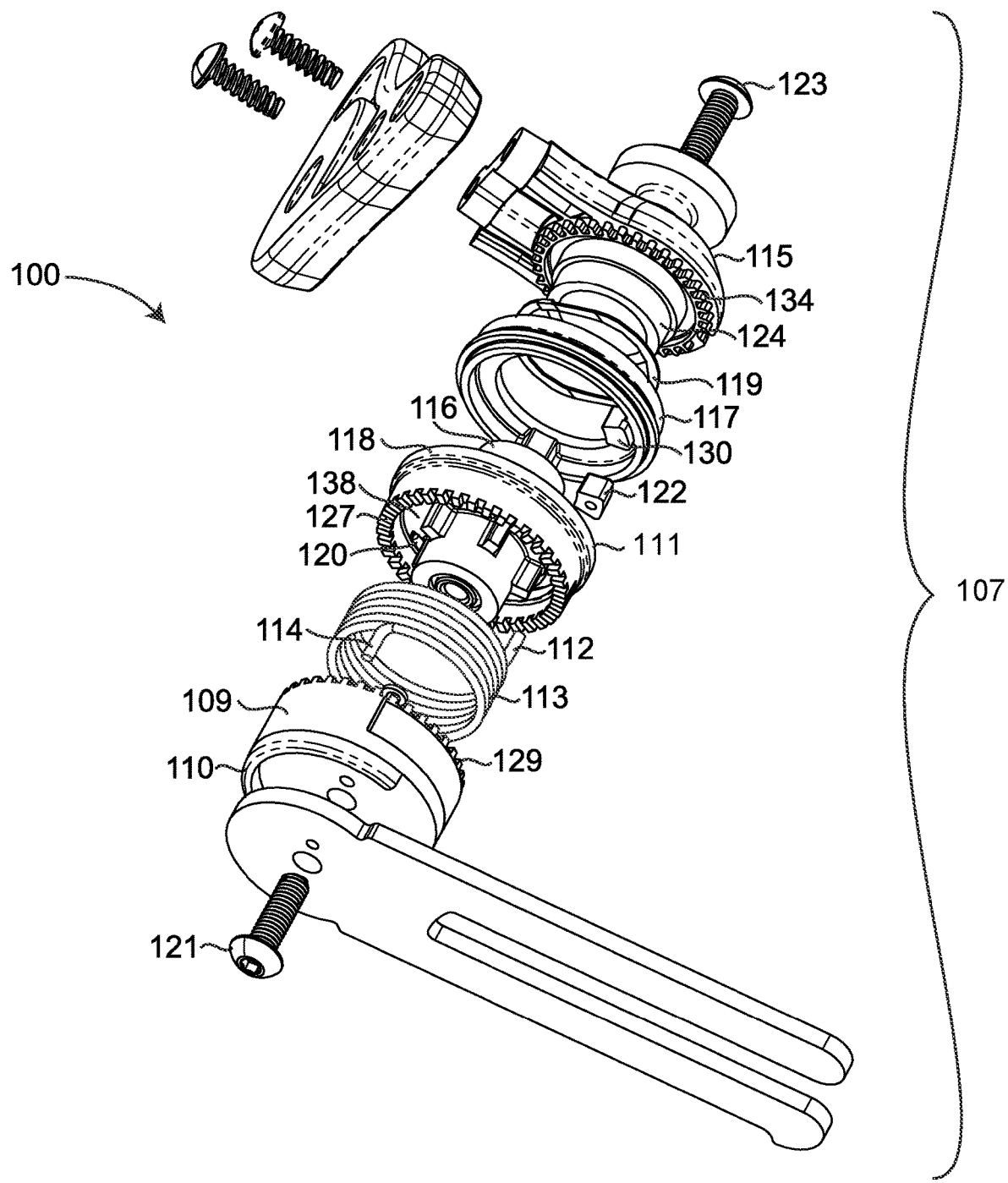
FIGS. 5A and 5B depict exploded isometric views of the device of FIG. 1 from an alternative perspective.
Figure 5B:
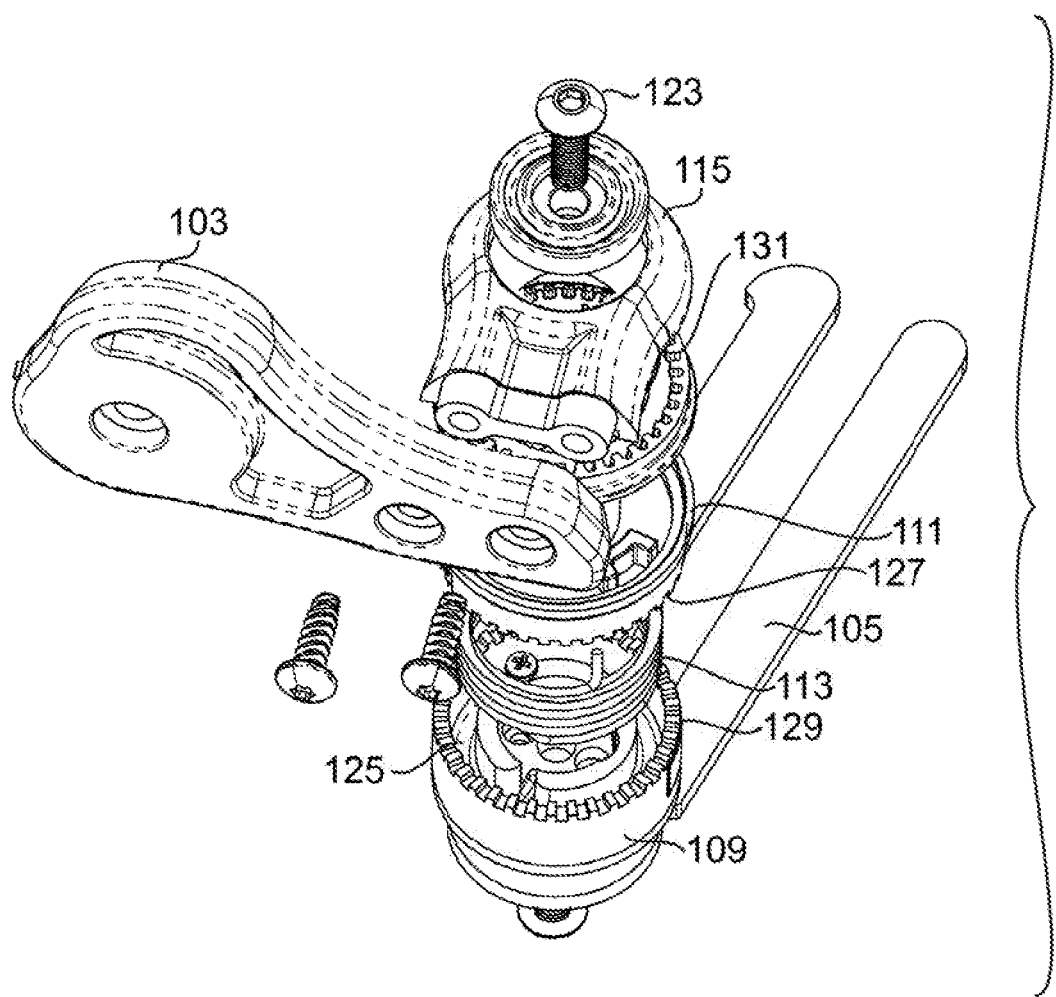

An exploded elevation view of an embodiment of a housing assembly (107) is depicted in FIG. 1, and an isometric exploded view from differing perspectives is shown in FIG. 2, FIG. 5A and FIG. 5B. An assembled view is shown in FIG. 3. The depicted housing assembly (107) comprises two different adjusting systems. One such adjusting system is a torque-adjusting system, and another such adjusting system is an orientation-adjusting system. Each of these two adjustment systems may be independently operated without full disassembly of the housing assembly (107).

The depicted torque-adjustment system comprises a base cap (109), a core cap (111), and a torsion spring (113). The depicted orientation-adjusting system comprises a core cap (111), a top cap (115), an index ring (117), and a wave spring (119). In the depicted embodiment, both the systems share at least one common element, the core cap (111). In an alternative embodiment, the systems may use independent components. However, to transfer torque, such as that applied by the torsion spring (113), to the paddle (103), there will be a physical transfer pathway through the housing assembly (107) to apply that force. In the depicted embodiment, this transfer pathway is provided by a top end (112) of the torsion spring (113) being situated within a spring stop (111) that is in turn received by the index ring (117).

The depicted base cap (109) is a generally cylindrical element adapted to attach to the torque bar (105). The bottom side of the depicted base cap (109) may have a protrusion (110) sized and shaped to fit into a corresponding recess in the torque bar. Alternatively, and as shown, the protrusion (110) may be an arcuate element, which partially circumscribes the distal end of the torque bar (105). This structure provides a firm connection, which inhibits rotation of the base cap (109) with respect to the torque bar (105). The base cap (109) may be attached to the torque bar (105) via hardware, such as a bolt or screw. This top side of the depicted base cap (109) opposes the bottom side and comprises a ring of teeth (129) circumscribing the outer rim of the top side.

The interior of the depicted base cap (109) is partially hollow, and includes various structures for interfacing and connecting to other elements of the system. By way of example and not limitation, the depicted base cap (109) includes an axial bore sized and shaped to accept a hex lock (121). Also, the depicted base cap (109) includes a hollow annular receiver (125) sized and shaped to receive a portion of a torsion spring (113), and a second generally cylindrical receiver (133) therein to receive the bottom end of the torsion spring (113).

These structures retain the bottom of the torsion spring (113) in the base cap (109) and facilitate the application of torque via the torsion spring (113) by affixing the opposing top (112) and bottom (114) ends of the torsion spring (113) in the base cap (109) and the index ring (117), respectively. The end cap (109) may include a guide on the exterior circumference, which provides a visual indication of the relative or absolute torque settings of the tension spring (113) at various positions of the teeth (129) as they interlock with corresponding teeth (127) in the core cap (111). This aspect is described in further detail elsewhere herein.

The depicted torsion spring (113) is a cylindrical, wound spring having a top end (112) and an opposing bottom end (114). In the depicted embodiment, both ends (112) and (114) are turned at an angle such that they are generally parallel with the center axis of the torsion spring (113). The bottom end (114) is sized and shaped to insert snugly into the second receiver (133) within the base cap (109). The top protrusion (112) is likewise sized and shaped to fit snugly into a corresponding receiver in the index ring (117). In an embodiment, this may be done using a spring stop (122). The top end (112) may pass through a channel (120) or aperture (120) in the core cap (111) as described elsewhere herein. The function of these structures is to provide anchor points within the assembly (107) for the torsion spring (113) so that as the spring is tightened, its torque may be transmitted to the paddles (103), and other shapes and structures may also be used in an embodiment to accomplish this. For example, in another embodiment, the top (112) or bottom (114) end of the spring (113) may not be angled, but rather may be an annular end which, when installed, is adjacent a stopping surface within the base cap (109).

As will be familiar to a person of ordinary skill in the art, in the prior art, the torsion spring (113) must be replaced over time. Because orthotic devices are typically used to treat young children, as the child grows and gains strength, a stronger spring is required. Using the structures described herein, rather than changing the spring, the amount of torque applied by the spring can be adjusted using the device without disassembling it.

Also shown is a core cap (111). The depicted core cap (111) is a generally cylindrical element having an inner column (116) partially circumscribed by a generally annular outer column (118). The inner column (116) has a radius smaller than that of the outer column (118), and contains opposing axial bores for receiving two locks (123) and (121), which assemble and lock the device (100). The depicted outer column (118) has a top outer rim sized and shaped to mate to a corresponding bottom rim of the index ring (117), and an opposing toothed (127) bottom rim sized and shaped to interlock with the teeth (129) of the base cap (109).

The depicted core cap (111) also comprises an arcuate aperture (120). The depicted arcuate channel (120) is co-radial and coaxial with the core cap (111) and wide enough to accommodate the passage of the top end (112) of the torsion spring (113). This facilitates independent operation of the two adjusting systems, while providing for transmission of the force of the tension spring (112) to the paddle (103) by allowing the top end (112) of the torsion spring (113) to pass through the arcuate channel (120) and connect to a spring stop (122) with the index ring (117). The arcuate shape of the channel (120) allows the core cap (111) to rotate axially through a range of motion without interfering with the connection of the torsion spring (113) to the index ring (117).

Figure 4A:
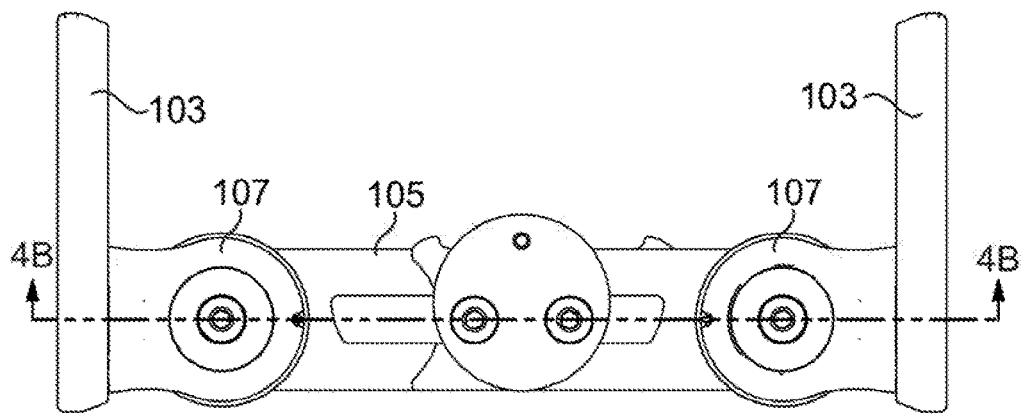
FIGS. 4A and 4B depict a cross-sectional elevation view of the assembled device of FIG. 1.
Figure 4B:
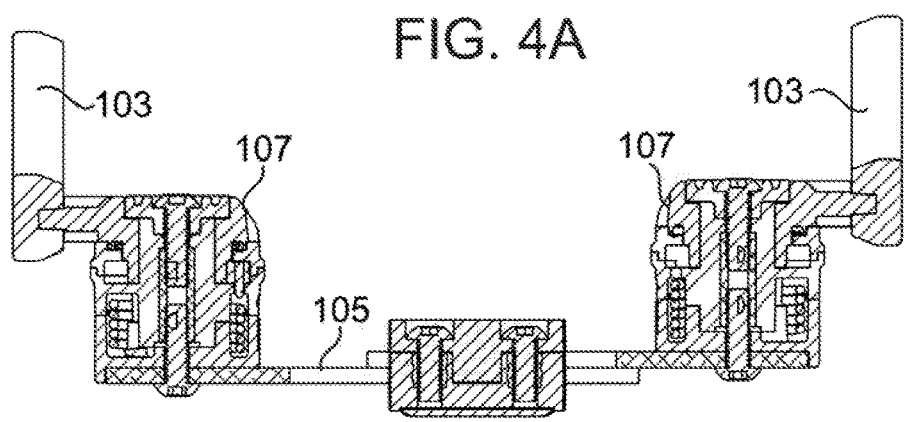

In an embodiment, the interior of the outer column (118) may be partially hollow and may include an annular recess in the bottom side sized and shaped to accept a portion of the torsion spring (113). This recess can be seen in the cross-section of FIG. 4A and FIG. 4B. This recess, when combined with the recess in the base cap (109), are generally large enough to fully enclose the torsion spring (113). Thus, the dimensions and configuration of the base cap (109), the core cap (111), and the torsion spring (113) may be selected to facilitate both the mating of the teeth (129) of the base cap (109) with those (127) of the core cap (111) while also enclosing the torsion spring (113) within the assembled structure. This arrangement also can be seen in FIGS. 4A and 4B.

Also depicted is an embodiment of an adjusting system for the orientation of the paddles (103). The depicted system comprises the core cap (111), the index ring (117), a wave spring (119), and the top cap (115). This system is assembled by first assembling the torsion spring (113) within the base cap (109) and core cap (111) so the top end (112) extends through the arcuate channel (120) and is received in a spring stop (122). The spring stop (122) may be received within a corresponding receiver in the bottom of the index ring (117), also to facilitate the transmission of torque to the paddle (103).

The depicted index ring (117) is a generally annular element having a bottom rim sized and shaped to mate with the top rim of the outer column (118) of the core cap (111). In this configuration, the center column (116) of the core cap (111) passes through a central opening of the index ring (117) and protrudes through a top side thereof. The radius of the center column (116) is smaller than the radius of the central opening in the index ring (117). This produces an annular gap approximately the same as that of an annular connecting element (124) of the top cap (115). The device (106) is thus assembled by passing this connecting element (124) through the centered opening in the index ring (117) to circumscribe the center column (116). An end cap may be placed within a recess or other receiving structure on top of the top cap (115).

The depicted core cap (111) may also comprise a receiver (126) sized and shaped to accept a locking protrusion (128) of the index ring (117). The depicted index ring (117) has, in addition to a receiver (130) for the spring stop (122), a locking protrusion (128) extending downwardly from the bottom surface of the index ring (117). This locking protrusion (128) is sized and shaped to correspond to a locking receiver (126) disposed on the top surface of the outer column (118) of the end cap (111). This connection assists with maintaining a rigid relationship between the elements and provides additional strength.

The orientation-adjusting mechanism also comprises a wave spring (119) disposed between the index ring (117) and the top cap (115) when the device is assembled. The wave spring (119) assists with torque adjustments by applying expansive pressure between the index ring (117) and top cap (115), causing these elements to disengage when the fastening hardware is loosened. The depicted index ring (117) top surface has a set of teeth (131) circumscribing a center opening thereof. Situated between the center opening and teeth (131) is a flat annular surface (132) sized and shaped to receive the wave spring (119). Thus, when the orientation-adjusting mechanism is assembled, the index ring (117) is fitted to the top of the outer column (118) of the core cap (111) by fitting the locking protrusion (128) into the locking receiver (126). The wave spring (119) is then placed on the flat annular surface (132) of the index ring (117), and the top cap (115) is attached so that its connecting element (124) passes through both the center openings of the wave spring (119) and index ring (117) to surround the inner column (116). An end cap may be placed into a receiver in the top cap (115). The end cap may also be received by an axial bore in the core cap (111) for additional structural rigidity. The depicted top cap (115) also has a ring of teeth (134) dispensed about the outer bottom rim and sized and shaped to interlock with the teeth (131) of the index ring (117).

Once all elements of the housing assembly (107) are connected, the housing assembly (107) is held in place by hardware. The dual-adjustment feature is facilitated by a pair of opposing hex locks (123) and (121). A bottom hex lock (121) is inserted through an aperture in the bottom of the torque bar (105) and protrudes through an axial bore in the base cap (109), to screw into a corresponding receiver (138) in the bottom of the core cap (111). Conversely, the top hex lock (123) is inserted downwardly into an axial bore through the top cap (115) to screw into a corresponding receiving bore in the center column (116). This has the effect of causing the lock to also pass through the axial center of the wave spring and index spring. To adjust either system, the physician merely loosens the appropriate lock (121) or (123) sufficiently for the applicable sets of teeth to disengage, rotates the element requiring adjustment, resets the teeth, and then tightens the lock.

For example, to tighten the tension, the physician may loosen the bottom lock (121) sufficiently for the teeth (127) and (129) to disengage, rotate the index ring (117) and core cap (111) to tighten the spring, re-engage the teeth (127) and (129) in a new position, and tighten the lock (121). To adjust the orientation, the physician loosens the top lock (123) sufficiently for the teeth (134) and (131) to disengage, adjusts the angle of the paddle (103) by adjusting the position of the top cap (115) with respect to the index ring (117), then re-engages the teeth (134) and (131), and tightens the lock (123). Alternatively, both nuts can be loosened at the same time and both systems may be adjusted.

Figure 6A:
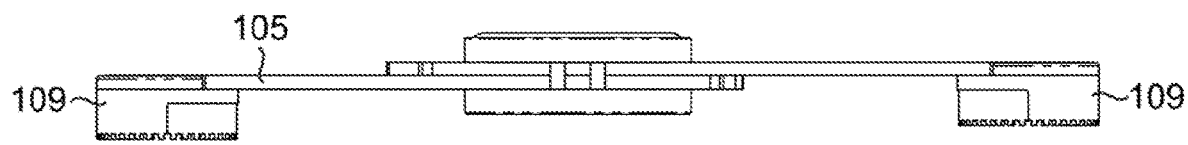
FIGS. 6A, 6B, 6C, and 6D depict a views of a long bar for mounting a pair of orthotic clubfoot paddles according to the present disclosure.
Figure 6B:
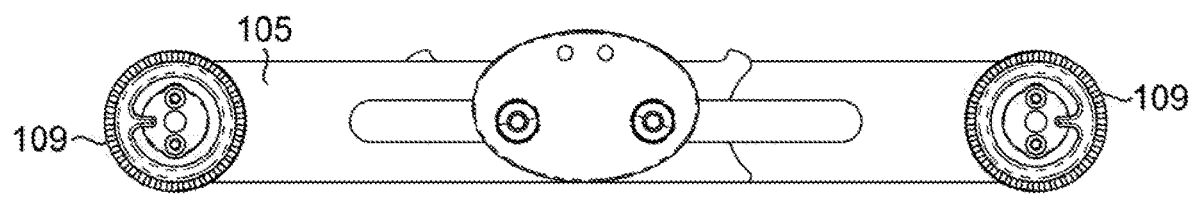
Figure 6C:
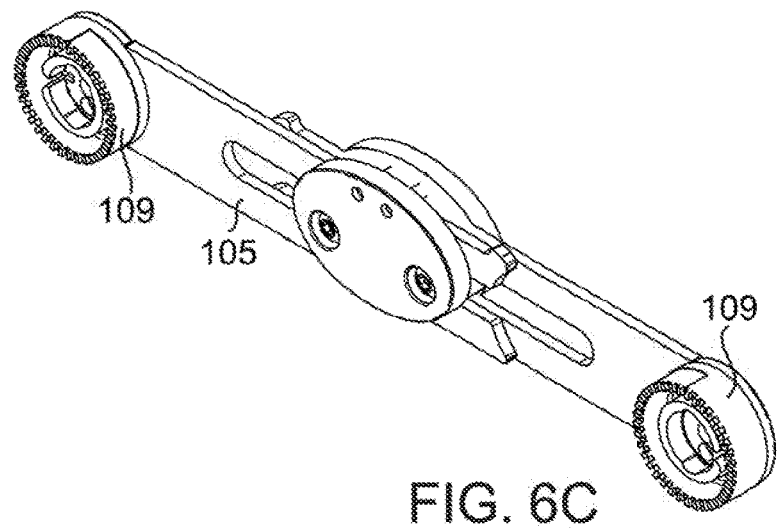
Figure 6D:
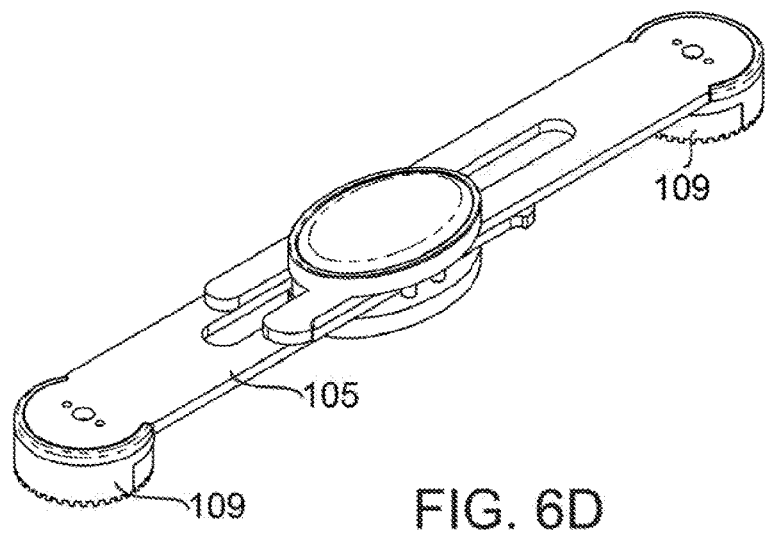

In the depicted embodiment, the torque bar (105) is comprised of two sections slideably attached in an adjustable configuration that facilitates a variable-length configuration along the major axis. An embodiment of such a torque bar (105) is depicted in FIGS. 6A to 6B, showing base caps attached thereto.

Throughout this disclosure, geometric terms may be used to characterize, among other things, sizes, shapes, dimensions, angles, distances, and relationships. These terms may be used with qualifiers such as "generally," "about," and "approximately." One of ordinary skill in the art will understand that, in the context of this disclosure, these terms are used to describe a recognizable attempt to conform a device or component to the qualified term. By way of example and not limitation, components described as being "generally coplanar" will be recognized by one of ordinary skill in the art to not be actually coplanar in a strict geometric sense because a "plane" is a purely geometric construct that does not actually exist and no component is truly "planer," nor are two components ever truly coplanar. Variations from geometric descriptions are unavoidable due to, among other things, manufacturing tolerances resulting in shape variations, defects, imperfections, non-uniform thermal expansion, natural wear, minor variations that are nevertheless recognizable as the qualified term, and other deformations. One of ordinary skill in the art will understand how to apply geometric terms, whether or not qualified by relative terms such as "generally," "about," and "approximately," to describe a reasonable range of variations from the literal geometric term in view of these and other considerations appropriate to the context. Additionally, the use of the conjunctive and disjunctive should not necessarily be construed as limiting, and the conjunctive may include the disjunctive, and vice versa.

Although the orthotic device is primarily disclosed herein with respect to clubfoot treatment and correction, this is not a limiting disclosure and the device and methods described herein are suitable for use in other contexts where the dual-adjustable housing assembly provides for independent adjustment of torque and angle without full disassembly of the apparatus or replacement of internal components.

While the invention has been disclosed in conjunction with a description of certain embodiments, including those that are currently believed to be the preferred embodiments, the detailed description is intended to be illustrative and should not be understood to limit the scope of the present disclosure. As would be understood by one of ordinary skill in the art, embodiments other than those described in detail herein are encompassed by the present invention. Modifications and variations of the described embodiments may be made without departing from the spirit and scope of the invention.

The invention claimed is:

1. A dual-adjustable housing assembly comprising:
 a base cap having a first plurality of teeth on a top periphery thereof;
 a core cap comprising:
  an inner column;
  an outer column having a radius larger than said inner column and a height shorter than said inner column, and a top side and an opposing bottom side, said bottom side having a second plurality of teeth on a periphery thereof, said second plurality of teeth intermeshing with said first plurality of teeth;
 an index ring having a bottom side disposed on said outer column top side so that said inner column passes through said index ring, and an opposing top side having a third plurality of teeth on a periphery thereof;
 a torsion spring having a bottom end in connection with said base cap and an opposing top end in connection with said index ring, said torsion ring applying an amount of torque to said index ring, said amount of torque corresponding to a first rotational position of said index ring relative to said base cap;

a top cap comprising:
   a radial protrusion adapted to accept a paddle; and
   a fourth plurality of teeth on a bottom periphery of said top cap, said fourth plurality of teeth intermeshing with said third plurality of teeth such that said radial protrusion is disposed at a first rotational angle to a vertical axis of said housing assembly, said first rotational angle corresponding to a first rotational position of said top cap relative to said index ring;

where when said index ring is rotated to a second rotational position relative to said base cap, said torsion spring applies a second amount of torque to said index ring corresponding to said second rotational position of said index ring relative to said base cap; and wherein when said top cap is rotated to a second rotational position relative to said index ring, said radial protrusion rotates to a second rotational angle corresponding to said second rotational position of said top cap relative to said index ring.

2. The dual-adjustable housing assembly of claim 1, further comprising a wave spring disposed between said index ring and said top cap.

3. The dual-adjustable housing assembly of claim 1, further comprising:
   a receiver disposed on said outer column top side; and
   a locking protrusion extending from said index ring bottom side and disposed in said receiver;
   wherein said locking protrusion disposed in said receiver causes said index ring and said core cap to rotate in concert.

4. The dual-adjustable housing assembly of claim 3, wherein said outer column comprises an arcuate aperture.

5. The dual-adjustable housing assembly of claim 4, wherein:
   a bottom portion of said torsion spring is disposed within a base cap receiver within an interior volume of said base cap;
   said bottom end of said torsion spring is disposed within a second receiver within said base cap receiver;
   a top portion of said torsion spring is disposed within a receiver within an interior volume of said outer column; and
   said top end passes through said arcuate aperture and is disposed in a receiver in said index ring.

6. The dual-adjustable housing assembly of claim 5, wherein said arcuate aperture is sized and shaped such that said index ring may be rotated to a plurality of rotational positions relative to said base cap while said top end is disposed through said arcuate aperture.

7. The dual-adjustable housing assembly of claim 1, further comprising a spring stop disposed in a receiver in said index ring and said top end of said torsion spring disposed in said spring stop.

8. An orthotic treatment device including a torque bar, a first dual-adjustable housing assembly affixed to a first end of said torque bar, and a second dual-adjustable housing assembly affixed to an opposing second end of said torque bar, wherein each of first dual-adjustable housing assembly and said second dual-adjustable housing assembly comprise the dual-adjusting housing assembly of claim 1.

9. The orthotic treatment device of claim 8, wherein said orthotic treatment device is a clubfoot correction device.

* * * * *